`US005147358A`

United States Patent [19]
Remmler

[11] Patent Number: 5,147,358
[45] Date of Patent: Sep. 15, 1992

[54] CRANIAL FIXATION-DISTRACTION AND POSITIONING APPARATUS AND METHOD

[76] Inventor: Daniel J. Remmler, 2330 S. 17th St. #2, Lincoln, Nebr. 68502

[21] Appl. No.: 602,947

[22] Filed: Oct. 23, 1990

[51] Int. Cl.$^5$ .............................................. A61F 5/00
[52] U.S. Cl. ......................................... 606/57; 606/90
[58] Field of Search .............................. 606/54, 55–58, 606/69, 70, 71, 90, 105, 86; 602/17

[56] References Cited

U.S. PATENT DOCUMENTS

| | | |
|---|---|---|
| 1,747,434 | 2/1930 | Ghrist . |
| 1,857,503 | 4/1941 | Ghrist . |
| 2,238,869 | 4/1941 | Haynes ............................ 606/57 X |
| 2,238,870 | 4/1941 | Haynes . |
| 2,333,033 | 10/1943 | Mraz .................................... 606/57 |
| 2,372,866 | 4/1945 | Tofflemire . |
| 3,386,437 | 6/1968 | Treace ................................ 606/105 |
| 3,488,779 | 1/1970 | Christensen ..................... 606/71 X |
| 3,709,219 | 1/1973 | Halloran . |
| 3,866,607 | 2/1975 | Forsythe et al. ................. 606/105 |
| 4,045,678 | 8/1977 | Rickard . |
| 4,064,401 | 12/1977 | Marden . |
| 4,096,857 | 6/1978 | Cramer et al. . |
| 4,102,339 | 6/1978 | Weber et al. ..................... 606/105 |
| 4,256,112 | 3/1981 | Kopf et al. . |
| 4,349,017 | 9/1982 | Sayegh . |
| 4,475,546 | 10/1984 | Patton . |
| 4,502,473 | 3/1985 | Harris et al. . |
| 4,504,050 | 3/1985 | Osborne . |
| 4,541,422 | 9/1985 | Zbikowski . |

(List continued on next page.)

FOREIGN PATENT DOCUMENTS 0940756 7/1982 U.S.S.R. ............................. 606/56

OTHER PUBLICATIONS

Ekstrom, C., Henrikson, C. O., and Jensen, R., "Mineralization in the Midpalatal Suture After Orthodontic Expansion", *American Journal Orthod.*, vol. 71, No. 3 (Apr., 1977), pp. 449–455.

Persing, J. A., Babler, W. J., Nagorsky, M. J., Edgerton, M. T. and Jane, J. A., "Skull Expansion in Experimental Craniosynostosis", *Plastic and Reconstructive Surgery*, vol. 78, No. 5 (Nov. 1986), pp. 594–603.

Owen, A. H., III, "The Maxillary Sagittal Appliance: A Clinical Study", *American Journal of Orthodontics and Dentofacial Orthopedics*, vol. 91, No. 4 (Apr. 1987), pp. 271–285.

Pyka, W. R. and Nagel, D. A., "Use of the Ilizarov External Fixator for Tibial Lengthening: Case Report", *Contemporary Orthopaedics*, vol. 17, No. 2 (Aug. 1988), pp. 15–21.

Paley, D., "Current Techniques of Limb Lengthening", *Journal of Pediatric Orthopaedics*, vol. 8, No. 1 (1988), pp. 73–92.

Ilizarov, G. A., "The Tension–Stress Effect on the Genesis and Growth of Tissues", *Clinical Orthopaedics and Related Research*, No. 238 (Jan. 1989), pp. 249–281.

(List continued on next page.)

*Primary Examiner*—Robert A. Hafer
*Assistant Examiner*—Brian E. Hanlon
*Attorney, Agent, or Firm*—Marshall, O'Toole, Gerstein, Murray & Bicknell

[57] ABSTRACT

A skull distraction and monitoring apparatus and method includes multiple mini-fixation plates fixedly attached to a craniofacial skeleton of a rabbit on either side of the coronal suture. Tubular members are fixedly attached to the plates. A distraction portion of the apparatus is fixedly attached to the tubular members. The distraction portion includes jackscrew assemblies that traverse the coronal suture and span thereabove. When the jackscrew assemblies are turned, the distraction portion of the apparatus expands, distracting an anterior skull portion and facial portion of the rabbit from the remainder of the skull. The distraction portion also includes registration apertures that are adapted to cooperate with a skull positioning assembly for repeatedly holding a skull in a particular position so that the skull expansion may be accurately monitored. A method for surgically attaching the apparatus, expanding the skull and monitoring skull expansion is described.

15 Claims, 3 Drawing Sheets

U.S. PATENT DOCUMENTS

| | | | |
|---|---|---|---|
| 4,561,266 | 2/1985 | McDaniel | 606/90 |
| 4,612,930 | 9/1986 | Bremer . | |
| 4,848,368 | 7/1989 | Kronner . | |
| 4,895,141 | 1/1990 | Koeneman et al. . | |
| 4,929,247 | 5/1990 | Rayhack . | |
| 4,936,843 | 6/1990 | Sohngen | 606/57 X |
| 4,941,481 | 7/1990 | Wagenknecht . | |
| 4,957,495 | 9/1990 | Kluger | 606/58 |

OTHER PUBLICATIONS

Green, S. A., "Ilizarov Orthopedic Methods", *AORN Journal*, vol. 49, No. 1 (Jan. 1989), pp. 215–230.

Kendra, J. C., Price, C. T., Songer, J. E., Scott, D. S., "Pediatric Applications of Dynamic Axial External Fixation", *Contemporary Orthopaedics*, vol. 19, No. 5, (Nov. 1989), pp. 477–486.

Schwartsman, V., McMurrary, M. R., and Martin, S. N., "The Ilizarov Method—The Basics", *Contemporary Orthopaedics*, vol. 19, No. 6 (Dec. 1989), pp. 628–638.

Karp, N. S., Thorne, C. H. M., McCarthy, J. G. and Sissons, H. A., "Bone Lengthening in the Craniofacial Skeleton", *Annals of Plastic Surgery*, vol. 24, No. 3, (Mar. 1990), pp. 231–237.

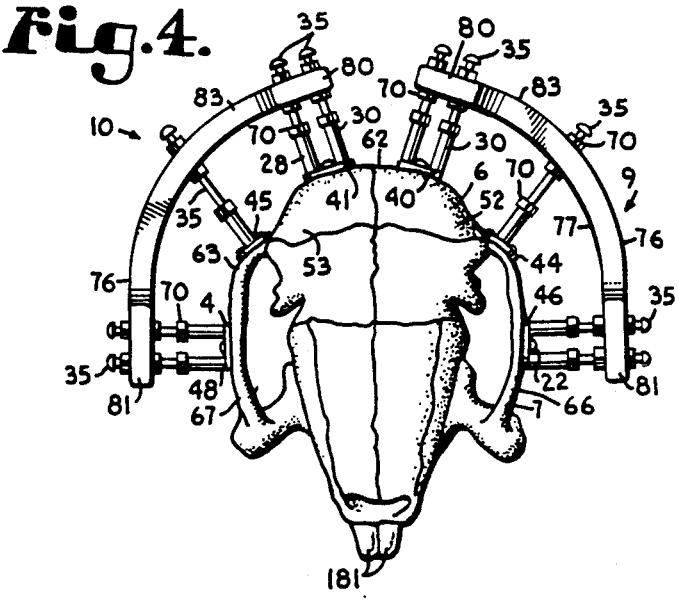
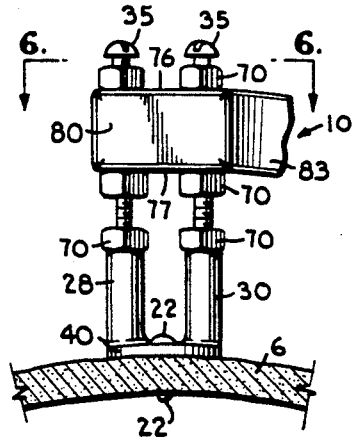
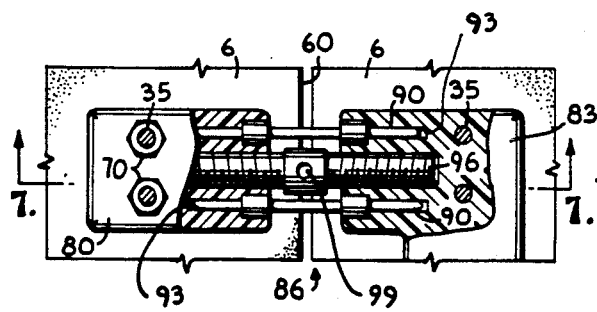
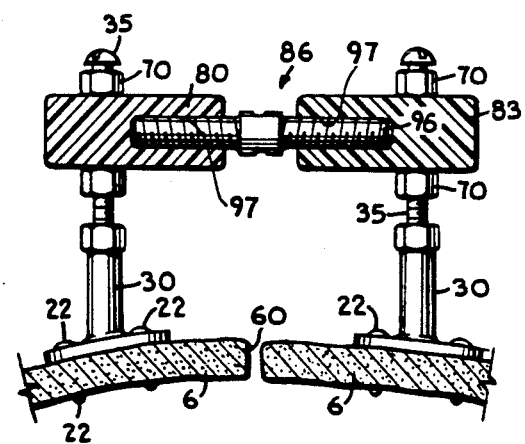

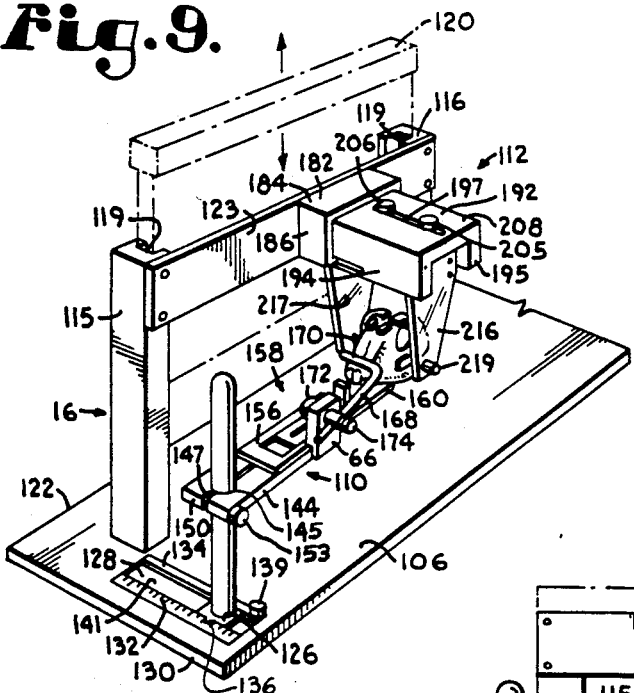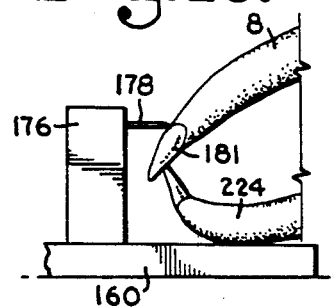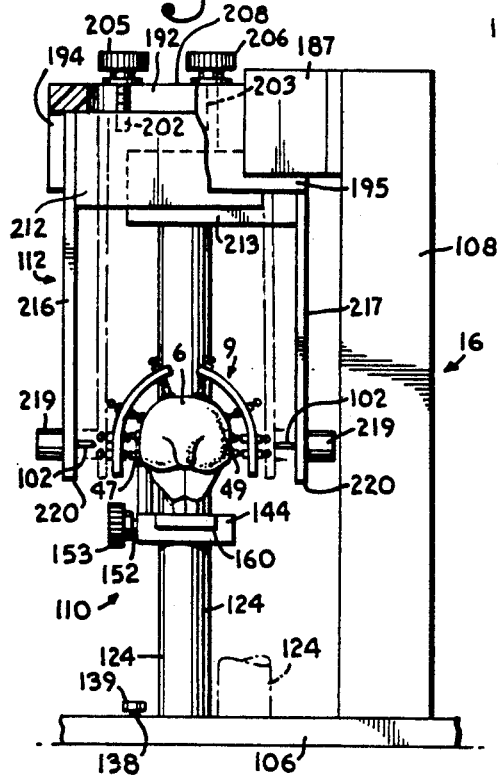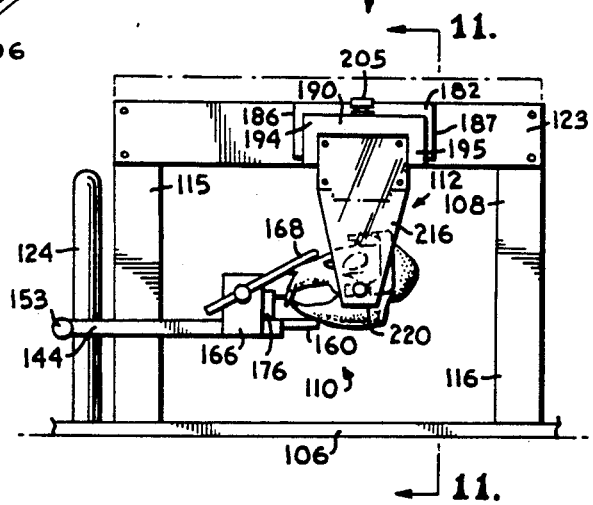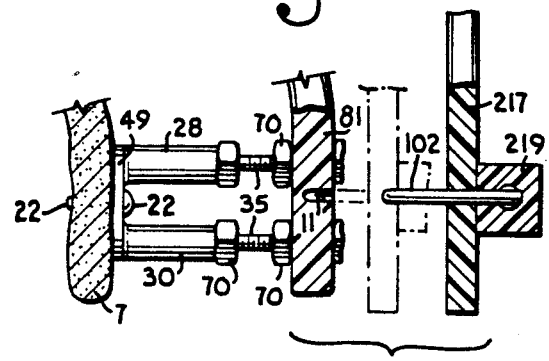

CRANIAL FIXATION-DISTRACTION AND POSITIONING APPARATUS AND METHOD

BACKGROUND OF THE INVENTION

The present invention relates to bone distraction and, more particularly, to an apparatus and method for osseous expansion of the skull and monitoring the same.

In human children, premature synostosis (fusion) of the coronal suture (the line of union of the two parietal bones with the frontal bone of the skull) causes a spectrum of craniofacial malformations ranging from simple brachycephaly to more severe deformities, such as Crouzon's and Apert's syndromes. The more severe deformities may also include premature fusion of the cranial base. These malformations display marked retrusion of the anterior cranial vault, anterior cranial base and facial skeleton. Left untreated, these deformities worsen, rather than improve, with continued skull growth.

There are several surgical procedures currently used to correct these anomalies. One method includes strip craniectomy release of all the fused sutures as early as possible in life to unharness the rapid brain growth of infancy. Theoretically, the skull then expands to proper relationship with the brain growth, thereby normalizing skull and facial growth. There is some evidence that this procedure has been successful when the fusion is simple and confined to the coronal suture system. Unfortunately, it has been unsuccessful in definitively correcting more extensive deformities such as Apert's and Crouzon's syndromes. Clinical evidence has indicated that in these severe anomalies, the forward push of the growing brain is unable to advance the retruded facial skeleton.

Thus, reconstructive advancement of the retruded facial skeleton in Apert's and Crouzon's syndromes is frequently deferred until early or mid-childhood when the facial skeleton is stronger and donor bone graft material present. Major craniofacial advancement is then accomplished by surgically disengaging and immobilizing the facial and frontal bones into a more anterior position with the use of multiple bone grafts. However, secondary operations are often required to maintain proper facial balance and dental occlusion.

A method that has been largely unexamined is to perform an initial interventive surgical release of the fused sutures and then apply continuous adjunctive external forces to the skull to distract the cranial bones. The forces should be congruent with the normal forward propulsive effort of the growing brain and be continuously regulated to guide the released craniofacial complex into the desired position. It is theorized that the widened intersutural spaces would be filled and stabilized with newly deposited bone.

Clinical techniques of facial sutural expansion have been confined mainly to the maxilla. Devices are available that apply forces across the mid-palatal suture to rapidly expand constricted maxillary dental arches and enlarge nasal airways. The devices deliver a transverse expansion force across the palate of children and adolescents by utilizing a jackscrew mechanism orthodontically fixed to the maxillary teeth. In adults, the immobile palatal sutures are surgically released prior to fixation of the device. The widened mid-palatal suture eventually fills with newly deposited bone. The facial sutural expansion method occurs most reliably when the periosteum enveloping the mid-palatal suture has been preserved.

Devices available for use with larger bone segments have generally focused on bone fixation to prevent skeletal relapse after fracture, rather than for the production of new bone between the segments. Fixation devices for stabilizing long bones typically include rods and coupling mechanisms attached to different parts of a fractured bone that hold the fractured bone parts together.

Devices are also available for use in the distraction of long, tubular bone sections that are externally fixed across a previously divided portion of the bone. The devices include pins or projections that extend deeply into the bone on either side of the divide and a mechanism for slowly expanding the device, thereby slowly elongating the bone. Once the desired length is achieved, the bone reconsolidates, resulting in both a solid union and lengthened limb.

Analogous application of such bone-expanding apparatus and methods have not been pursued in the field of surgical reconstruction of synostotic deformities. This delay may, in part, be due to the slow development of a suitable animal model for the study of craniosynostosis. Only relatively recently, such an animal model, rabbits, has been reported.

Furthermore, as stated above, the application of bone-expanding apparatus and methods to the area of skull expansion should include the careful application of force congruent with the normal forward propulsive effort of the growing brain which would require continuous regulation to guide the released craniofacial complex into the desired position. Regulation of bone growth necessitates a device for precisely monitoring the same. Radiographic techniques adequately provide an image of the skull and newly-formed bone, but precise monitoring of the bone expansion requires that a portion of the skull be repeatably placed in precisely the same position relative to the radiographic equipment.

Devices are available for humans that register an entire skull, with respect to medical equipment, by utilizing inserts for placement in the ears or contoured members that receive the head or facial features. These devices are not appropriate for monitoring skull expansion where a portion of the face or skull is being lengthened. Such devices would fail to register the skull with respect to one of the skull sections and, therefore, may not provide the preciseness required for tracking incremental bone growth. Additionally, devices created for adult humans may not be readily adapted for use with children, whose facial features may rapidly change, or for use with other animals, such as rabbits, for example, who do not have prominent facial features or ear openings placed for receipt of immobilizing projections. Therefore, there is a need for a registration and positioning device to be utilized with a skull fixation-distraction apparatus that is not dependent upon an outer feature of the patient being monitored.

SUMMARY OF THE INVENTION

A skull fixation-distraction and monitoring apparatus and method disclosed in this application is utilized to slowly distract a rabbit skull at the coronal suture and monitor resultant newly deposited bone in the widened intersutural spaces. The apparatus includes a fixation portion and a distraction portion. The fixation portion includes mini-fixation plates that are fixedly attached to a skull of a rabbit with self-tapping screws. Each fixation plate has two tubular members fixedly attached thereto and extending generally perpendicular therefrom.

The distraction portion includes left and right bar assemblies that are generally U-shaped and contoured to follow the curvature of the head and face of a rabbit. The bar assemblies include screws extending therethrough that are positioned and adapted to mate with the tubular members of the fixation portion of the invention. Each bar assembly includes two jackscrew devices encased therein that are located on each leg of the U-shaped assembly. Each bar assembly also includes a registration aperture.

A total of ten fixation plates are affixed to a rabbit's skull and facial skeleton with two generally aligned frontal fixation plates affixed on the skull anterior to the coronal suture and two coordinating generally aligned rear fixation plates affixed to the skull posterior to the coronal suture. Left and right rear fixation plates are mounted on the squamous portion of the temporal bone on either side of the rabbit's skull and two left facial and two right facial fixation plates are placed on either side of the facial skeleton at the zygomatic arch.

The fixation plates are surgically attached to the skull with the tubular members extending outwardly, away from the skull. The overlying soft tissues are then closed, covering the plates and tubular members and the incisions are allowed to heal. The open end of each tubular member is then exteriorized by means of an overlying small stab incision.

The right bar assembly is then fixedly attached to the tubular members of one frontal, one rear, the right rear and the two right facial fixation plates and the left bar assembly is fixedly attached to the tubular members of one frontal, one rear, the left rear and the two left facial fixation plates. The jackscrews span between the frontal and parietal bones and the cheekbone and the squamous portion of the temporal bone. As the jackscrews are slowly and equally expanded, the skull is distracted in the area of the coronal suture and new bone is deposited in the widened coronal suture space.

Skull expansion is monitored utilizing the registration apertures in the distraction portion of the apparatus in cooperation with a holding and positioning structure. The structure includes a generally flat, horizontal rectangular base with a vertical radiograph holder mounted at one edge thereof. A telescoping anterior support is slidingly attached to the base so that the space between the anterior support and radiograph holder may be adjusted and recorded to enable the operator to repeatedly radiograph a particular rabbit from the same lateral distance. The anterior support may also be adjusted vertically and includes a lower jaw support adapted for the placement of a rabbit's lower jaw thereon and a locating pin that is adapted to fit between the incisors of a rabbit placed thereupon. Also, an L-shaped bar is rotatably mounted on the anterior support and is adapted for positioning upon a rabbit's face above the nasal bone, thereby vertically holding a rabbit between the lower jaw support and the L-shaped bar.

A skull positioning assembly is attached to an upper portion of the radiograph holder and extends laterally and generally horizontally therefrom. The skull positioning assembly includes a pair of slidable generally vertical, members. A pin is mounted on each member perpendicular thereto and is adapted to project into a registration aperture of a bar assembly of the distraction portion of the apparatus. The vertical members may be adjusted laterally, thereby adapted to center over the anterior support and restrict the horizontal movement of a rabbit when both pins are inserted in a distraction portion of the apparatus that has been mounted on a rabbit. The skull positioning assembly and cooperating registration apertures thereby hold the anterior portion of the skull in the same position each time a radiograph is taken of a particular rabbit, providing precise monitoring of the extent of expansion of the coronal suture.

OBJECTS AND ADVANTAGES OF THE INVENTION

Therefore, the objects of the present invention are: to provide a continuous and controllable apparatus and method for guiding normal craniofacial growth; to provide such a method and apparatus that may avert functional and cosmetic deformities of coronal synostosis; to provide such a method and apparatus that may lead to providing a normal craniofacial growth in human children and largely obviate the need for extensive craniofacial osteotomies and bone grafts; to provide a method of continuous normal craniofacial growth that depends solely on the consolidation of newly deposited intersutural bone for stability; to provide an expandable external fixation-distraction device utilized on rabbits applied to advance the anterior cranium and midface as a unit; to provide such a device that may lead to use on children to advance the anterior cranium and midface as a unit following strip craniectomy release of fused coronal sutures; to provide such a device that includes small plates that are fixedly attached to the skull of a patient and includes tubular members extending percutaneously; to provide such an apparatus that includes relatively simple expansion assemblies attached to the tubular members; to provide an apparatus and method that accurately monitors the slow consolidation of newly deposited bone; to provide such an apparatus and method that includes a monitoring structure that cooperates with the fixation-distraction device in accurately measuring the expansion of the skull; to provide such a fixation-distraction device and monitoring structure that is relatively easy to mount on a skull, relatively inexpensive to construct and particularly well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 4 is an enlarged, front elevational view of the fixation-distraction and registration portion, shown attached to a rabbit skull.

FIG. 5 is an enlarged and fragmentary, front elevational view of the fixation-distraction and registration portion, shown attached to a rabbit skull.

FIG. 6 is an enlarged and fragmentary, cross-sectional view of the fixation-distraction and registration portion, taken along 6—6 of FIG. 5 and shown attached to a rabbit skull.

FIG. 7 is an enlarged and fragmentary, cross-sectional view of the fixation-distraction and registration portion and rabbit skull, taken along 7—7 of FIG. 6.

FIG. 8 is an enlarged and fragmentary, side elevational view of the fixation-distraction and registration portion, shown attached to a rabbit skull.

FIG. 9 is a reduced, perspective view of the fixation-distraction and registration portion, shown with a rabbit skull and held by a positioning and holding portion of the apparatus according to the present invention.

FIG. 10 is a reduced, side elevational view of the apparatus and rabbit skull.

FIG. 11 is a reduced, cross-sectional view of the apparatus and rabbit skull, taken along 11—11 of FIG. 10.

FIG. 12 is an enlarged and fragmentary, front elevational view of the apparatus and rabbit skull with the positioning and holding portion shown connected to the fixation-distraction and registration portion, in phantom lines, and disconnected from the fixation-distraction and registration portion, in solid lines.

FIG. 13 is an enlarged and fragmentary, side elevational view of the positioning and holding portion and rabbit skull.

DETAILED DESCRIPTION OF THE INVENTION

Figure 1:
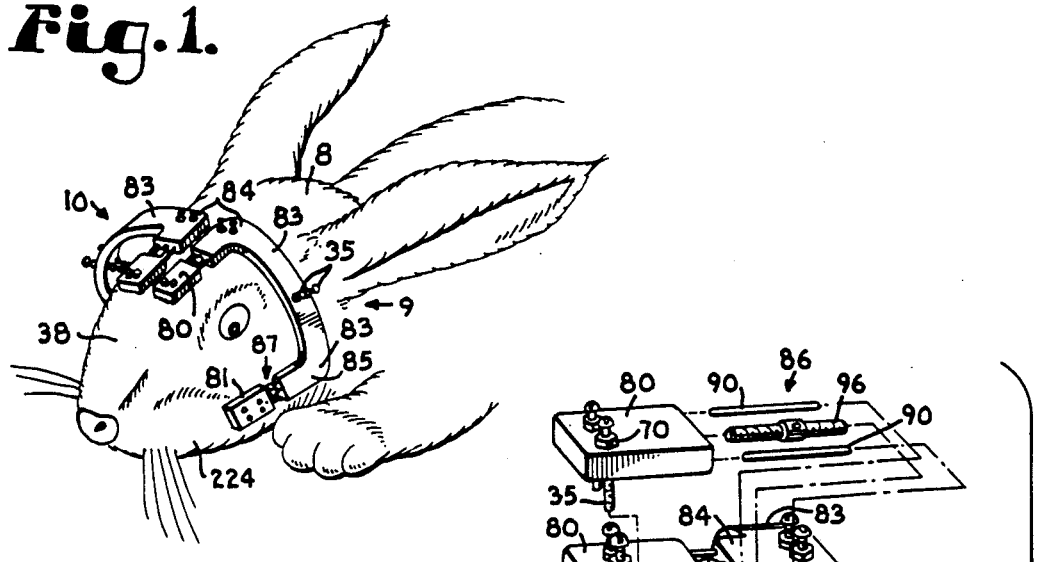
FIG. 1 is a perspective view of a skull fixation-distraction and registration portion of an apparatus according to the present invention, shown attached to a rabbit.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in detail, a cranial fixation-distraction and positioning apparatus of this invention, generally designated by the reference numeral 1 includes a skull fixation means or portion illustrated by mini-fixation plates 4, adapted for mounting on a skull 6 and facial skeleton 7 of a rabbit 8, a skull distraction means or portion illustrated by support bar assemblies 9 and 10, registration means illustrated by apertures 11 and 13 and skull holding means or portion illustrated by a holding and positioning structure 16.

Figure 2:
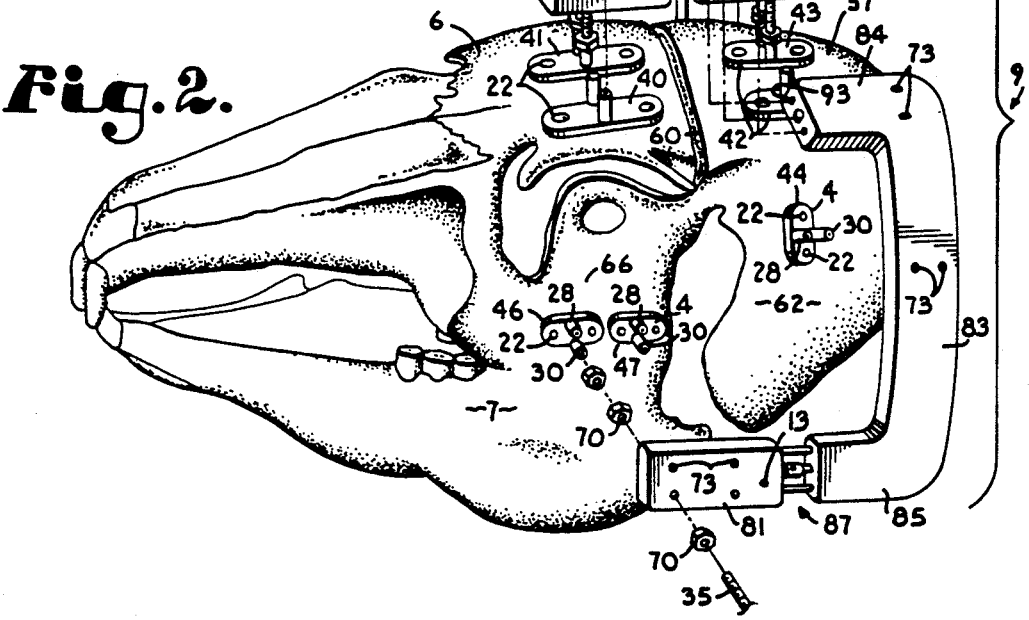
FIG. 2 is an enlarged, exploded perspective view of the fixation-distraction and registration portion, shown attached to a rabbit skull.
Figure 3:
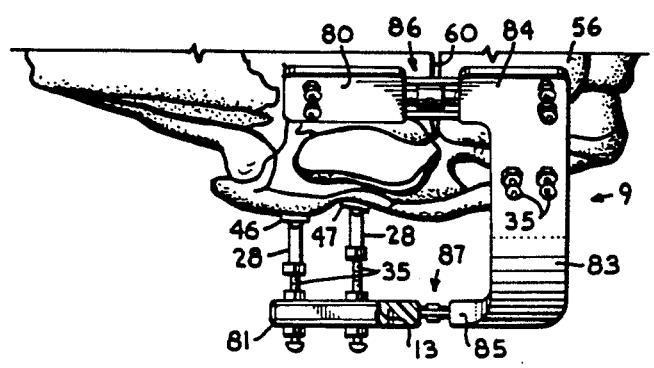
FIG. 3 is an enlarged, fragmentary, top plan view of the fixation-distraction and registration portion, shown attached to a rabbit skull.

Referring particularly to FIGS. 1 through 8, each mini-fixation plate 4 is generally flat and oblong in shape and includes two apertures 19 located at either end thereof through which self-tapping screws 22 extend. Screws 22 also extend through apertures 25 previously drilled into the rabbit skull 6 or facial skeleton 7 and thereby fixedly attach each plate 4 to the skull 6 or facial skeleton 7.

First and second generally identical tubular members 28 and 30 are fixedly mounted to each fixation plate 4 between apertures 19 and project perpendicularly from plate 4. The inner tubular surface 33 of members 28 and 30 is threaded and adapted to receive screws 35 that are also fixedly connected to a skull distraction portion 9 or 10. Tubular members 28 and 30 are sized to extend above a rabbit's skin 38 when a plate 4 is mounted on a skull 6 or facial skeleton 7. The fixation plates 4 and attached tubular members 28 and 30 are made from metal but it is foreseen that other strong materials may be utilized for making the same. It is advantageous, however, for the fixation plates 4 to be made of radiopaque material to allow for tracking of the skull distraction by radiographic methods.

A total of ten fixation plates 4 are mounted onto the skull 6 and facial skeleton 7 of a rabbit 8 for the apparatus 1 and process of the disclosed invention. In order to describe the locations of the fixation plates 4, each shall hereafter be numbered as plates 40, 41, 42, 43, 44, 45, 46, 47, 48 and 49 and the particular coordinating location described.

Fixation plate 40 is located on the left frontal skull bone 52, plate 41 on the right frontal skull bone 53, plate 43 on the left parietal bone 56 and plate 44 on the right parietal bone 57. Plates 40 and 42 are generally aligned and approximately equally distanced from the coronal suture 60. Plates 41 and 43 are generally aligned and approximately equally distanced from the coronal suture 60. Plates 40 and 41 and plates 42 and 43 are also respectively aligned generally transverse to the alignment between plates 40 and 42 and plates 41 and 43 respectively. Tubular members 28 and 30 of plates 40 and 41 are generally aligned and tubular members 28 and 30 of plates 42 and 43 are generally aligned.

Plate 44 is located on the squamous portion of the left temporal bone 62 and plate 45 is the mirror image of plate 44 and located on the squamous portion of the right temporal bone 63. Apertures 19 of plates 44 and 45 respectively are generally vertically aligned with tubular members 28 and 30 of each of plates 44 and 4 aligned generally horizontally.

Plates 46 and 47 are located on the left zygomatic arch or cheekbone 66 and are generally in horizontal alignment with plate 46 anterior to plate 47. Plates 48 and 49 are the mirror image of plates 46 and 47 and are located on the right zygomatic arch or cheekbone 67 and are generally in horizontal alignment with plate 48 anterior to plate 49. Tubular members 28 and 30 of each of plates 46, 47, 48 and 49 are in vertical alignment.

The support bar assemblies 9 and 10 of the skull distraction portion of the apparatus 1 are mirror images with assembly 9 located generally on the left side of the skull 6 and facial skeleton 7 of the rabbit 8 and assembly 10 located generally on the right side of the skull 6 and facial skeleton 7 of the rabbit 8. Ten screws 35 and thirty cooperating locking nuts 70 fixedly attach support bar assembly 9 to tubular members 28 and 30 of fixation plates 40, 42, 44, 46 and 47. Ten screws 35 and thirty cooperating locking nuts 70 fixedly attach assembly 10 to fixation plates 41, 43, 45, 48 and 49. The screws 35 extend through apertures 73 of assemblies 9 and 10 with locking nuts 70 abutting thereagainst at an outer surface 76 and an inner surface 77 and abutting against tubular members 28 and 30, keeping assemblies 9 and 10 spaced from the fixation plates 4 and spaced generally equally above the rabbit skin 38. Each assembly 9 and 10 is generally U-shaped and contoured such that the entire assembly is approximately equally spaced from the rabbit 8.

Each assembly 9 and 10 includes anterior, generally horizontally-positioned legs or bars 80 and 81 and a curved, posterior end member 83 having generally horizontally-positioned shoulders 84 and 85.

Jackscrew assemblies 86 and 87 connect end member 83 with legs 80 and 81 respectively. When assembly 9 is mounted onto fixation plates 4, jackscrew assembly 86 spans between the left frontal bone 52 and the left parietal bone 56 across the coronal suture 60 and jackscrew assembly 81 spans between the cheekbone 66 and the left temporal bone 62. When assembly 10 is mounted onto fixation plates 4, jackscrew assembly 86 spans between the right frontal bone 53 and the right parietal bone 57 across the coronal suture 60 and jackscrew assembly 81 spans between the cheekbone 67 and the right temporal bone 63.

Each of the jackscrew assemblies 86 and 87 includes a pair of support bars 90 slidingly mounted in apertures 93 of legs 80 and 81 and shoulders 84 and 85. A screw member 96 is received by threaded apertures 97 in legs 80 and 81 and shoulders 84 and 85 of end member 83. Member 96 is threaded and has a slot 99 adapted to receive a small wrench (not shown) for the purpose of turning screw member 96 within apertures 97 and thereby pushing end member 83 either toward or away from anterior leg 80 or leg 81 depending upon the direction member 96 is turned.

Each leg 81 also includes a registration means, illustrated by apertures 11 and 13, that is adapted to receive generally horizontally-oriented pins 102 mounted to the holding and positioning structure 16. Tubular members 28 and 30 of fixation plates 46, 47, 48 or 49 may also be adapted for receiving pins 102 when a radiograph is taken of a rabbit that has not had assemblies 9 or 10 mounted thereupon. In the alternative, small fixation buttons (not shown) adapted to receive tubular members 28 and 29 and having an aperture may be mounted on either plates 46 and 48 or plates 47 and 49 with the aperture of each button adapted to receive a pin 102.

The holding and positioning structure 16, illustrated in FIGS. 9-12, generally includes a flat, rectangular base 106, radiograph holder means, illustrated by a generally vertical radiograph holder 108, fixedly attached to base 106, telescoping lower support means, illustrated by an anterior support 110, slidingly attached to the base 106 and adjustable skull positioning means, illustrated by a skull positioning assembly 112.

The radiograph holder 108 includes a pair of spaced identical vertical legs 115 and 116, each having a groove 119 for the placement of a radiograph 120 therebetween. Each leg 115 and 116 is welded or otherwise fixedly attached to base 106 near an edge 122 thereof. A top support beam 123 that is generally parallel to edge 122 is fixedly attached to both leg 115 and leg 116.

The anterior support 110 includes a generally vertical, cylindrical post 124 that is attached to a generally flat, rectangular sliding base 126. Base 106 includes a recessed slot 128 that receives base 126. Slot 128 runs parallel to edge 130 of base 106 and is transverse to radiograph holder 108. A rectangular ruler frame 132 opposite of a rectangular holding frame 134, is located at either edge of slot 128 and holds sliding base 126 within slot 128. The sliding base includes a raised indicator 136 fixedly connected thereto so that an operator may measure the distance between the anterior support 110 and the radiograph holder 108. The post 124 may be slid to a desired position along slot 128 and secured in that position by the tightening of a fastening pin 138 that extends through base 106 and includes a head 139 that presses down upon frame 134 which in turn frictionally holds sliding base 126 between frame 134 and a bottom surface 141 of slot 128.

A generally horizontal and rectangular support 144 having an aperture 145 adapted to slidingly receive post 124 is mounted thereon. The support 144 includes a longitudinal slot 147 that extends to an edge 150 of the support 144. A fastening pin 152 also extends horizontally through support 144 near edge 150 and includes a fastening knob 153 integral thereto. When knob 153 is turned, the edges of slot 147 are pulled together, causing aperture 145 to constrict about post 124, thereby frictionally holding support 144 at a desired vertical distance from base 106.

A first, nontelescoping portion 156 of a telescoping lower jaw support 158 is fixedly attached to support 144 and extends in a direction parallel to radiograph holder 108. A telescoping portion 160 is slidingly attached to portion 156 and is framed and received thereby. Telescoping portion 160 is slidingly seated on top of support 144 and adapted for holding the lower jaw of a rabbit thereon. A holding pin (not shown) extends vertically through nontelescoping portion 156 and support 144 and includes a fastener (not shown) that abuts against the telescoping portion 160 and nontelescoping portion 156, thereby holding the telescoping portion 160 in fixed horizontal placement when the fastener is frictionally tightened against portions 156 and 160. Telescoping portion 160 may be slidingly adjusted in a direction parallel to radiograph holder 108 to provide adequate support for a rabbit's jawbone. It is noted that, although FIGS. 9-13 show apparatus 1 utilized with a rabbit skull 6, the holding and positioning structure 16 is primarily for use with a live rabbit 8.

A first mounting block 166 is fixedly attached to support 144. An L-shaped bar 168 is rotatably mounted thereto. A transverse leg 170 of the bar 168 is adapted for placement upon a rabbit's face above the nasal bone, thereby vertically holding a rabbit between the telescoping portion 160 of the lower jaw support 158 and leg 170. The L-shaped bar 168 may be locked into a desired position by turning fastener 172 that frictionally abuts a pivot pin 174 through which bar 168 extends against mounting block 166.

A second mounting block 176 is fixedly attached to the telescoping portion 160 of the lower jaw support 158. An indicator pin 178 extends horizontally from block 176 in a direction parallel to radiograph holder 108. Pin 178 is adapted to be positioned between the incisors 181 of the rabbit 8. Pin 178 is slidingly mounted on block 176 such that it may be adjusted vertically and that it may telescope toward the rabbit incisors 181. Fasteners (not shown) hold the pin 178 in a desired position.

The skull positioning assembly 112 includes a first support section 182 that is fixedly attached to top support beam 123 and extends generally transversely thereupon and away from radiograph 120. Support section 182 includes a planar horizontal member 184 and two planar vertical members 186 and 187.

A second support section 190 also includes a planar horizontal member 192 and two planar vertical members 194 and 195. The second support section 190 is slidingly attached to section 182 with section 190 partially inserted in section 182 with member 184 adjacent to member 192, member 186 adjacent to member 194 and member 187 adjacent to member 195. Support section 190 extends generally transversely from the radiograph holder 108.

Horizontal member 192 includes a slot 197 that is also transverse to the radiograph holder 108. Two threaded pins 202 and 203 extend vertically through slot 197 and are fixedly attached to knobs 205 and 206 respectively that abut against a top surface 208 of member 192. Pin 202 extends into a threaded aperture in a Plexiglas block 212 that is located within support section 190 and is suspended from pin 202. Pin 203 extends into a threaded aperture in a Plexiglas block 213 that is also located within support section 190 and is suspended from pin 203. Blocks 212 and 213 are sized and positioned such that pins 202 and 203 are easily and freely slidable within slot 197.

First and second generally flat, planar, vertical skull positioning plates 216 and 217 are fixedly attached to blocks 212 and 213 respectively and are suspended therefrom. Each of plates 216 and 217 are positioned parallel to edge 122 of base 106 and are spaced to receive a rabbit head therebetween. Positioning pins 102 having outer knobs 219 are fixedly attached to each of plates 216 and 217 near a lower edge 220 thereof. The pins 102 each face toward the lower jaw support 158. The lateral position of plates 216 and 217 may be adjusted by sliding pins 202 and 203 along slot 197, utilizing knobs 205 and 206 with the knobs frictionally abutting against surface 208.

The support section 182, support section 190, blocks 212 and 213, vertical plates 216 and 217, pins 102 and knobs 219 are made from clear materials, such as Plexiglas, that do not obstruct the passage of radiographic waves therethrough. The L-shaped bar 168, telescoping portion 160 of lower jaw support 158 and indicator pin 178 are also made from such material.

To operate the apparatus 1 of the present invention on rabbits, the following surgical steps must first be taken: a transverse coronal incision is made on the rabbit and skin flaps are elevated anteriorly and posteriorly in the subperiosteal plane. An incision is also made over the left and right zygoma. Holes are drilled in the skull 6 and facial skeleton 7 to be received by self-tapping screws 22 for attaching fixation plates 4 thereto at locations corresponding to the selected placement of fixation plates 40 through 49 described above. Fixation plates 40 through 49 are then attached to the skull 6 and facial skeleton 7 by screwing screws 22 thereinto. Plugs are placed in the tubular members 28 and 30 so that fibrous tissue does not grow therein. The incisions are then closed and allowed to heal.

After the wounds heal, the tubular members 28 and 30 are exteriorized by making small stab incisions in the rabbit skin at each tubular member location. The skin is pushed down about the tubular members 28 and 30 so that members 28 and 30 are located percutaneously.

Support bar assembly 9 is then attached to tubular members 28 and 30 of fixation plates 40, 42, 44, 46 and 47 utilizing ten screws 35 and thirty locking nuts 70. Support bar assembly 10 is attached to tubular members 28 and 30 of fixation plates 41, 43, 45, 48 and 49 utilizing ten screws 35 and thirty locking nuts 70.

The jackscrew assemblies 86 and 87 located on both support bar assembly 9 and 10 are then equally turned at a slow rate between one and two millimeters each week thereby expanding support bar assemblies 9 and 10 and forcing distraction of the skull along the coronal suture 60. The widened suture 60 then fills in with newly deposited bone 222 as shown in FIG. 8.

Suture and skull growth are followed by utilizing the skull holding and positioning structure 16 to hold a rabbit while a radiograph is taken. A rabbit having support bar assemblies 9 and 10 mounted thereon is placed on base 106 with the lower jaw 224 placed on the telescoping portion 160 of the lower jaw support 158. The L-shaped bar 168 is rotated about pivot pin 174 to a position where leg 170 is on top of the rabbit's nasal bone. Indicator pin 178 is placed between the rabbit's incisors 181 and pins 102 are positioned within registration apertures 11 and 13. Knobs 153, 172, 205 and 206 are then tightened to securely hold the rabbit 8 in a generally aligned position spaced from the radiograph holder 108. The position of indicator 136 with respect to ruler frame 132 is recorded so that the rabbit may be positioned at the same distance from the radiograph holder 108 each time a radiograph 120 is taken. Repeated radiographs are taken of the rabbit over a period of at least nine weeks. Growth of bone 222 at the coronal suture 60 is then recorded as the change in separation of the radiopaque fixation plates 4 located at either side of the coronal suture 60.

It is to be understood that while certain forms of the present invention have been illustrated and described herein, it is not to be limited to the specific forms or arrangement of parts described and shown.

What is claimed and desired to be secured by Letters Patent is as follows:

1. An apparatus for distracting a first portion of an animal skull from a second portion thereof and for holding the skull in a precise position relative to monitoring equipment; said apparatus comprising;
    (a) skull fixation means adapted to be fixedly attached directly to the first and second portions of the skull and to extend percutaneously and outwardly therefrom;
    (b) skull distraction means adapted to be spaced from the skull and to fixedly mate with said fixation means; said distraction means being adapted to span the first and second portions of the skull; said distraction means being adapted to be slowly expanded forcing distraction of the first and second skull portions resulting in the deposition of new bone in the widened space between the first and second skull portions;
    (c) registration means located on said distraction means; and
    (d) skull holding means adapted to slidingly attach to said registration means.

2. An apparatus according to claim 1 wherein said skull fixation means includes:
    (a) a fixation plate adapted to be located contiguous to the skull; said fixation plate having a first aperture;
    (b) a first screw extending through said first aperture and adapted to be fixedly attached to the skull; and
    (c) a tubular member having an upper portion; said tubular member fixedly attached to said fixation plate and adapted to extend percutaneously and outwardly therefrom away from the skull.

3. An apparatus according to claim 2 wherein said skull distraction means includes;
    (a) a support bar spaced from said fixation plate; said support bar having a second aperture;
    (b) a second screw adapted to be received by both said tubular member and said support bar and fixedly attaching said fixation plate to said support bar; and
    (c) a jackscrew encased by said support bar adapted for slowly distracting the first portion of the skull from the second portion.

4. The apparatus according to claim 3 wherein:

(a) said registration means includes said second aperture.

5. An apparatus for distracting an anterior portion of an animal skull and a facial skeleton portion forwardly from a posterior portion of the skull and depositing new bone at a cranial suture therebetween; said apparatus comprising;
   (a) first fixation means adapted for attachment to the anterior portion of the skull;
   (b) second fixation means adapted for attachment to the facial skeleton;
   (c) third fixation means adapted for attachment to the posterior portion of the skull; and
   (d) skull distraction means adapted to be fixedly attached to said first, second and third fixation means; said distraction means adapted to expand and force said third fixation means away from both said first and said second fixation means.

6. The apparatus according to claim 5 wherein said skull distraction means includes:
   (a) a first and second bar member adapted to be located on opposite sides of the facial skeleton; each of said bar members having a registration aperture.

7. The apparatus according to claim 6 including:
   (a) a base;
   (b) a radiograph holder fixedly attached to said base;
   (c) a telescoping lower support slidingly attached to said base and selectively spaced from said rediograph holder; and
   (d) adjustable skull positioning means connected to and spaced from said radiograph holder and adapted to be received by said registration apertures.

8. The apparatus according to claim 5 including:
   (a) a fourth fixation means adapted to be attached to the anterior portion of the skull and adapted for being fixed to said skull distraction means.

9. The apparatus according to claim 8 wherein said skull distraction means includes;
   (a) a support bar assembly adapted to be spaced from said first, second and third fixation means;
   (b) a first jackscrew attached to said support bar assembly and adapted to span said first fixation means and said third fixation means; and
   (c) a second jackscrew attached to said support bar assembly and adapted to span said second fixation means and said fourth fixation means.

10. An apparatus for distracting an anterior portion of an animal skull and facial skeleton portion forwardly from a posterior and a temporal portion of the skull and depositing new bone at a cranial suture therebetween and for holding the skull at a precise position relative to monitoring equipment; said apparatus comprising:
    (a) a first fixation plate assembly adapted to be attached to the anterior portion of a skull;
    (b) a second fixation plate assembly adapted to be attached to the facial skeleton;
    (c) a third fixation plate assembly adapted to be attached to the posterior portion of the skull;
    (d) a fourth fixation plate assembly adapted to be attached to the temporal portion of the skull;
    (e) a U-shaped distraction bar assembly fixedly attached to said first, second, third and fourth fixation plate assemblies; said distraction bar assembly having:
       (1) a first generally horizontally oriented anterior leg;
       (2) a second generally horizontally oriented anterior leg having an aperture; and
       (3) a generally vertically oriented posterior end member;
    (f) a first jackscrew assembly fixedly attached to said first leg and said posterior end member and located between said first fixation plate and said third fixation plate;
    (g) a second jackscrew assembly fixedly attached to said second leg and said posterior end member and located between said second fixation plate and said fourth fixation plate;
    (h) a base;
    (i) a radiograph holder fixedly attached to said base;
    (j) a telescoping lower support slidingly attached to said base and selectively spaced from said radiograph holder; and
    (k) a skull holding and positioning assembly connected to and adjustably spaced from said radiograph holder and adapted for being inserted into said aperture.

11. A method for distracting a first portion of an animal skull from a second portion thereof, comprising the steps of:
    (a) making a transverse coronal incision on a head of the animal;
    (b) elevating the animal skin flaps anteriorly and posteriorly;
    (c) drilling a pair of holes in both the first and second portions of the skull;
    (d) attaching a fixation plate to each of the first and second skull portions by mounting screws into the holes and into apertures located on each fixation plate;
    (e) closing the incision and allowing the incision to heal;
    (f) exteriorizing tubular members attached to each fixation plate;
    (g) attaching a skull distraction assembly to the tubular members; and
    (h) expanding the skull distraction assembly.

12. An apparatus for distracting a first portion of an animal skull from a second portion thereof and for holding the skull in a precise position relative to monitoring equipment; said apparatus comprising:
    (a) skull fixation means adapted to be fixedly attached directly to the first and second portion of the skull and to extend percutaneously and outwardly therefrom;
    (b) skull distraction means adapted to be spaced from the skull and to fixedly mate with said fixation means; said distraction means being adapted to span the first and second portions of the skull; said distraction means being adapted to be slowly expanded forcing distraction of the first and second skull portions resulting in the deposition of new bone in the widened space between the first and second skull portions;
    (c) registration means located on said distraction means; and
    (d) skull holding means adapted to slidingly attach to said registration means; said skull holding means including
       (i) a base;
       (ii) radiograph holder means fixedly attached to said base;

(iii) telescoping lower support means slidingly attached to said base and selectively spaced from said radiograph holder means; and (iv) adjustable skull positioning means connected to and spaced from said radiograph holder means and adapted to be received by said registration means.

13. An apparatus according to claim 12 wherein said skull fixation means includes:

(a) a fixation plate adapted to be located contiguous to the skull; said fixation plate having a first aperture;

(b) a first screw extending through said first aperture and adapted to be fixedly attached to the skull; and (c) a tubular member having an upper portion; said tubular member fixedly attached to said fixation plate and adapted to extend percutaneously and outwardly therefrom away from the skull.

14. An apparatus according to claim 13 wherein said skull distraction means includes;

(a) a support bar spaced from said fixation plate; said support bar having a second aperture;

(b) a second screw adapted to be received by both said tubular member and said support bar and fixedly attaching said fixation plate to said support bar; and (c) a jackscrew encased by said support bar adapted for slowly distracting the first portion of the skull from the second portion.

15. The apparatus according to claim 14 wherein:

(a) said registration means includes said second aperture.

* * * * *